US00PP13928P39

(12) United States Plant Patent
Pieters

(10) Patent No.: US PP13,928 P3
(45) Date of Patent: Jul. 1, 2003

(54) CHRYSANTHEMUM PLANT NAMED 'GEDI ONE SAV'

(75) Inventor: Dirk Pieters, Staden (BE)

(73) Assignee: Pieters Plant Production, BVBA, Oostnieuwkerke (BE)

( * ) Notice: Subject to any disclaimer, the term of this patent is extended or adjusted under 35 U.S.C. 154(b) by 0 days.

(21) Appl. No.: 09/873,956

(22) Filed: Jun. 4, 2001

(65) Prior Publication Data

US 2002/0188981 P1 Dec. 12, 2002

(51) Int. Cl.[7] ..... A01H 5/00
(52) U.S. Cl. ..... Plt./293
(58) Field of Search ..... Plt./292, 293, 290, Plt./287

(56) References Cited

U.S. PATENT DOCUMENTS

PP10,208 P 1/1998 Pieters ..... Plt./289
PP10,213 P 1/1998 Wain ..... Plt./287

*Primary Examiner*—Bruce R. Campell
*Assistant Examiner*—June Hwu
(74) *Attorney, Agent, or Firm*—Knobbe, Martens, Olson & Bear, LLP

(57) ABSTRACT

A new and distinct Chrysanthemum plant variety characterized by a large, decorative type inflorescence, consistent flowering response to short days, blooming consistently after 49 days of short day length, free branching habit, and highly floriferous plants.

1 Drawing Sheet

LATIN NAME

*Dendranthema morifolium*

VARIETY

'Gedi One Sav'

BACKGROUND OF THE INVENTION

Figure 1:
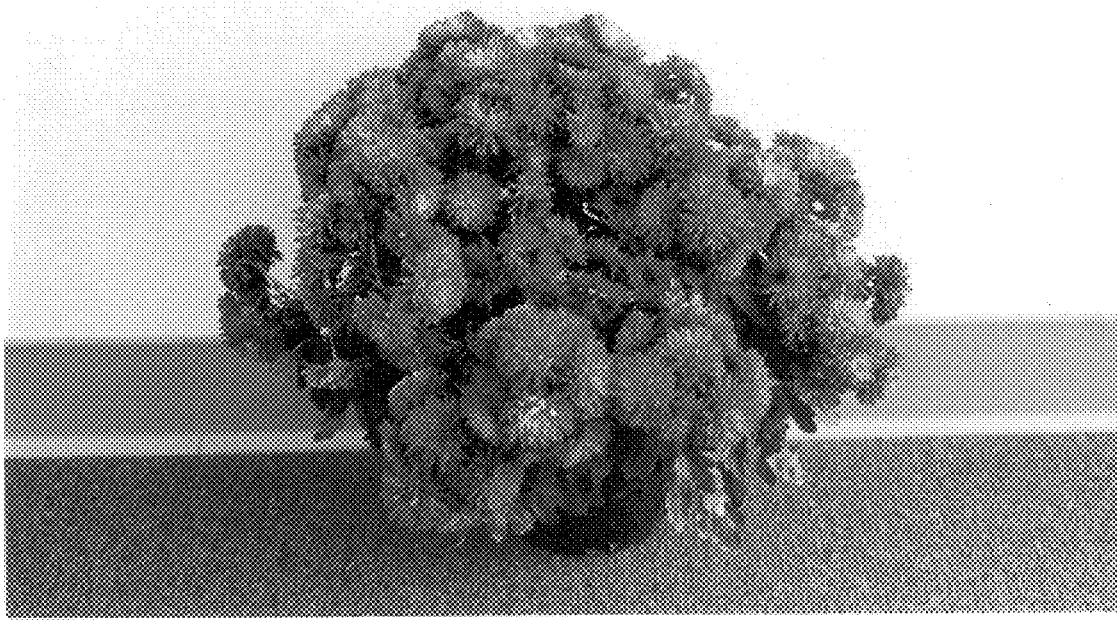

The present invention relates to a new and distinct cultivar of Chrysanthemum plant, botanically known as *Dendranthema morifolium* and herein after referred to by the cultivar name 'Gedi One Sav.'

This new cultivar originated from hybridization of a female plant, cultivar 'Pinos' (U.S. Plant Pat. No. 10,208), and a male parent, cultivar 'Maribelle' (unpatented in the United States). The new cultivar was discovered by the inventor in October 1996.

Asexual reproduction of the new cultivar by apical tip cutting and meristem tissue culture was performed in Oxnard, Calif. and has shown that the unique features of this new cultivar are stable and reproduced true to type on successive generations.

SUMMARY OF THE INVENTION

The cultivar 'Gedi One Sav' has not been observed under all possible environmental conditions. The phenotype may vary somewhat with variations in environment such as temperature, daylength, and light intensity, without, however, any variance in genotype.

The following traits have been repeatedly observed and are determined to be the unique characteristics of 'Gedi One Sav.' These observations were made on plants approximately 130 days old from rooted cuttings. These characteristics in combination distinguish 'Gedi One Sav' as a new and distinct Chrysanthemum:

1. Large, decorative type inflorescence;
2. Consistent flowering response to short days, blooming consistently after 49 days of short day length;
3. Free branching habit; and
4. Highly floriferous plants.

Plants of the variety 'Pinos' were grown next to the new cultivar 'Gedi One Sav' for this description. Differences from the patent description information given for 'Pinos' are due to different growing conditions. The 'Pinos' plant used for the patent description was grown in a greenhouse, with 5 cuttings in a pot, 'Gedi One Sav' and 'Pinos' used for this description were grown outdoors, with 1 cutting in a pot. Plants of the new cultivar are similar to plants of the parent cultivar, 'Pinos,' in most horticultural characteristics, however plants of the new cultivar differed from plants of the cultivar 'Pinos' in the following characteristics:

1. The new cultivar is taller and wider;
2. The new cultivar has larger diameter blooms; and
3. The new cultivar has different color ray florets.

Plants of the new cultivar are also similar to plants of the parent cultivar, 'Maribelle,' in most horticultural characteristics, however plants of the new cultivar differed from plants of the cultivar 'Maribelle' in the following characteristics:

1. The new cultivar has more ray florets;
2. The new cultivar has a more round, uniform plant shape; and
3. The new cultivar naturally blooms 2 week earlier.

Plants of the variety 'Jenny Wren' were grown next to the new cultivar 'Gedi One Sav' for this description. Differences from the patent description information given for Pinos are due to different growing conditions. The 'Jenny Wren' plant used for the patent description was grown in a greenhouse, with 5 cuttings in a pot, 'Gedi One Sav' and 'Jenny Wren' used for this description were grown outdoors, with 1 cutting in a pot. Plants grown outdoors over the course of the summer consistently develop more ray florets than those grown in a greenhouse over a shorter growing period.

The new cutivar can be compared to the Chrysanthemum cultivar 'Jenny Wren' (disclosed in U.S. Plant Pat. No. 10,213). However, plants of the new Chrysanthemum differed from the plants of the cultivar 'Jenny Wren' in the following characteristics:

1. The new cultivar has more ray florets;
2. The new cultivar has a more round plant shape and greater branching;
3. The new cultivar has a shorter internode length;
4. The new cultivar has a more flexible plant form; and
5. The new cultivar has more blooms per flowering branch.

BRIEF DESCRIPTION OF THE PHOTOGRAPHS

The photograph shows a plant of 'Gedi One Sav' grown in a 1-gallon container. A single cutting was used in the pot.

DETAILED BOTANICAL DESCRIPTION

In the following description, color references are made to The Royal Horticultural Society Colour Chart except where general terms of ordinary dictionary significance are used. The following observations and measurements describe plants grown in a commercial field in Oxnard, Calif. in the month of September 2000. The growing conditions range from 60° to 65° F. at night to 70° to 85° F. during the day. Measurements and numerical values represent averages of typical flowering types.

Botanical classification: *Dendranthema morifolium* cultivar 'Gedi One Sav'.
Commercial classification: Garden-type Chrysanthemum.
Parentage: Hybridization of female parent 'Pinos' (U.S. Plant Pat. No. 10,208) and male parent 'Maribelle' (unpatented in the United States).

Propagation

Time to rooting: 7 to 14 days at approximately 21° C.
Root description: Fine, fibrous.

Plant

Growth habit: Mounding herbaceous perennial.
Height: Approximately 22 cm.
Plant spread: Approximately 30 cm.
Growth rate: Moderate.
Branching characteristics: Free branching.
Internode length: Approximately 2.9 cm.
Length of lateral branches: Approximately 18 cm.
Number of leaves per lateral branch: Approximately 18.

Foliage

Leaf:
*Arrangement.*—Alternate, single.
*Average length.*—Approximately 5.4 cm.
*Average width.*—Approximately 3.4 cm.
*Shape of blade.*—Ovate.
*Apex.*—Acuminate.
*Base.*—Attenuate.
*Attachment.*—Stalked.
*Margin.*—Pinnately lobed and toothed.
*Texture of top surface.*—Lightly pubescent.
*Texture of bottom surface.*—Lightly pubescent.
*Color.*—Young foliage upper side: Near 147A. Young foliage under side: Near 147A. Mature foliage upper side: Near 147A. Mature foliage under side: Near 147A. Venation upper side: Near 148B. Venation under side: Near 147B.

Petiole:
*Average length.*—Approximately 2.0 cm.
*Color.*—Near 137A.
*Diameter: Approximately* 0.2 cm.

Bloom

Inflorescence:
*Flowering habit.*—Induced by darkness period greater than 13.5 hours, approximately 49 days of appropriate day length required to induce and develop blooms.
*Inflorescence form.*—Decorative.
*Natural flowering season.*—Approximately the first two weeks in September.
*Number of inflorescences per stem.*—Approximately 28.
*Inflorescence diameter.*—Approximately 4.7 cm.
*Inflorescence depth.*—Approximately 2.0 cm.
*Inflorescence longevity on plant.*—Approximately 24–27 days.
*Persistent.*—Persistent.

Ray florets:
*Appearance.*—Matte.
*Texture.*—Smooth.
*Average number per flower.*—Approximately 190.
*Shape.*—Cylindric.
*Margin.*—Entire.
*Apex.*—Obtuse.
*Length.*—Approximately 2 cm.
*Width.*—Approximately 0.5 cm.
*Color.*—Upper surface at first opening: Near 183A. Upper surface at maturity: Near 185A. Upper surface at fading: Near 182B. Under surface at first opening: Near 183C. Under surface at maturity: Near 184B. Under surface at fading: Near 182C.

As the ray florets begin to fade some streaks of 13D on the upper and lower surfaces.

Disc florets:
*Appearance.*—Shiny.
*Texture.*—Smooth.
*Average number per flower.*—Approximately 1 to 5.
*Shape.*—Cylindric.
*Apex.*—Obtuse.
*Average length.*—Approximately 0.2 cm.
*Average width.*—Approximately 0.1 cm.
*Color.*—At first opening: Near 154B. At maturity: Near 2A. At fading: Near 11A.

Peduncle:
*Length.*—At terminal end (shortest): Approximately 2.5 cm. At lateral end (longest): Approximately 2.8 cm.
*Diameter.*—Approximately 0.3 cm.
*Strength.*—Moderate.
*Color.*—Near 146A.
*Habit.*—Erect.
*Surface texture.*—Lightly pubescent.

Inflorescence bud:
*Length.*—Approximately 0.5 cm.
*Diameter.*—Approximately 0.5 cm.
*Form.*—Globular.
*Color.*—Near 137A.

Phyllaries:
*Appearance.*—Matte.
*Texture.*—Lightly pubescent.
*Number.*—Approximately 50 to 60.
*Shape.*—Ovate.
*Margin.*—Entire.
*Apex.*—Acute.
*Diameter.*—Approximately 0.2 cm.
*Length.*—Approximately 0.4 cm.
*Color.*—Upper side: Near 137B.
Under side.—Near 137B.

Reproductive Organs

Ray florets:
*Number of pistils per flower.*—1.
*Stigma shape.*—2 branched.
*Stigma color.*—Near 15A.
*Style length.*—Approximately 0.1 cm.
*Stamens.*—Absent.

Disc florets:
*Number of pistils per flower.*—1.
*Stigma shape.*—Cylindric.
*Style length.*—Approximately 0.2 cm.
*Number of stamens per flower.*—Approximately 5.
*Anther shape.*—Tubular.
*Anther color.*—Near 15A.
*Pollen color.*—Near 15A.

Other Characteristics

Seed production: Commercially, this plant is not used or observed in a stage wherein seeds would be produced. Therefore, seed production has not been observed.
Flower fragrance: Absent.
Disease resistance: Neither resistance nor susceptibility to diseases and pests have been observed in this cultivar.

What is claimed is:

1. A new and distinct variety of Chrysanthemum plant named 'Gedi One Sav' as herein illustrated and described.

* * * * *